(12) United States Patent
Smolander et al.

(10) Patent No.: US 7,785,894 B2
(45) Date of Patent: Aug. 31, 2010

(54) PACKAGE FOR ENCLOSING FOOD

(75) Inventors: Maria Smolander, Espoo (FI); Eero Hurme, Espoo (FI); Markku Koivisto, Kauniainen (FI); Sami Kivinen, Tampere (FI)

(73) Assignee: UPM Raflatac Oy, Tampere (FI)

( * ) Notice: Subject to any disclaimer, the term of this patent is extended or adjusted under 35 U.S.C. 154(b) by 718 days.

(21) Appl. No.: 10/557,002

(22) PCT Filed: Mar. 25, 2004

(86) PCT No.: PCT/FI2004/000166

§ 371 (c)(1),
(2), (4) Date: Nov. 27, 2006

(87) PCT Pub. No.: WO2004/102185

PCT Pub. Date: Nov. 25, 2004

(65) Prior Publication Data
US 2007/0087443 A1   Apr. 19, 2007

(30) Foreign Application Priority Data
May 16, 2003   (FI) .................................. 20030743

(51) Int. Cl.
*G01N 21/75* (2006.01)
(52) U.S. Cl. ................. 436/166; 436/1; 436/2; 436/164; 426/87; 426/112; 426/231; 426/232; 422/82.08; 422/82.07; 422/56; 422/57; 422/58; 422/61; 422/52; 422/86; 422/87; 116/206

(58) Field of Classification Search ....................... None
See application file for complete search history.

(56) References Cited

U.S. PATENT DOCUMENTS

| | | | |
|---|---|---|---|
| 2,626,855 A | 1/1953 | Hand | |
| 4,746,616 A * | 5/1988 | Honigs et al. | .................. 436/20 |
| 5,407,829 A | 4/1995 | Wolfbeis et al. | |
| 5,753,285 A | 5/1998 | Horan | |
| 6,149,952 A | 11/2000 | Horan | |

FOREIGN PATENT DOCUMENTS

| | | | |
|---|---|---|---|
| FI | 20012243 | | 5/2003 |
| JP | 2000056793 | | 9/2001 |
| WO | WO 9821120 A1 | | 5/1998 |
| WO | WO 00/13009 | * | 3/2000 |
| WO | WO 03044521 A1 | | 5/2003 |

OTHER PUBLICATIONS

Hawkins, et al., The use of thin silver film for the detection of low concentrates of hydrogen sulphide, 1998, Analytica Chimica ACTA, vol. 359, pp. 125-132.*

* cited by examiner

*Primary Examiner*—Yelena G Gakh
*Assistant Examiner*—Robert Xu
(74) *Attorney, Agent, or Firm*—Venable LLP; Eric J. Franklin

(57) ABSTRACT

An indicator that reacts with at least one gaseous compound in such a way that the color of the indicator is changed. The indicator is a layer formed on a substrate and including metallic silver and/or metallic copper.

10 Claims, 2 Drawing Sheets

PACKAGE FOR ENCLOSING FOOD

CROSS-REFERENCE TO RELATED APPLICATIONS

This application claims priority under 35 U.S.C. §119 to Finnish patent application no. 20030743 filed on 16 May 2003 and is the national phase application of PCT/FI2004/000166 under 35 U.S.C. §371.

FIELD OF THE INVENTION

The present invention relates to an indicator which reacts with at least one gaseous compound in such a way that the colour of the indicator is changed.

BACKGROUND OF THE INVENTION

The present invention relates to an indicator which reacts with at least one gaseous compound in such a way that the colour of the indicator is changed.

Publication WO 98/21120 discloses a myoglobin indicator reacting to hydrogen sulphide.

Publications U.S. Pat. No. 6,149,952 and U.S. Pat. No. 5,753,285 disclose an indicator colour combined with a hydrophilic polymer.

Publication U.S. Pat. No. 5,407,829 discloses the development of coloured sulphides from salts of heavy metals. The change in the colour is monitored visually or by means of optoelectonic devices.

Publication JP 2001238696 discloses an indicator intended for detecting *Salmonella* bacteria in eggs. The indicator is formed by adsorbing a silver, copper or mercury ion by a fibre substance. The indicator will react to gaseous compounds emitted from the egg by a change in the colour.

SUMMARY OF THE INVENTION

The indicator according to the invention is characterized in that the indicator is a layer formed on a substrate comprising metallic silver and/or metallic copper.

BRIEF DESCRIPTION OF THE DRAWINGS

In the following, the invention will be described with reference to the examples and FIG. 1.

DETAILED DESCRIPTION OF EMBODIMENTS OF THE INVENTION

Figure 1:
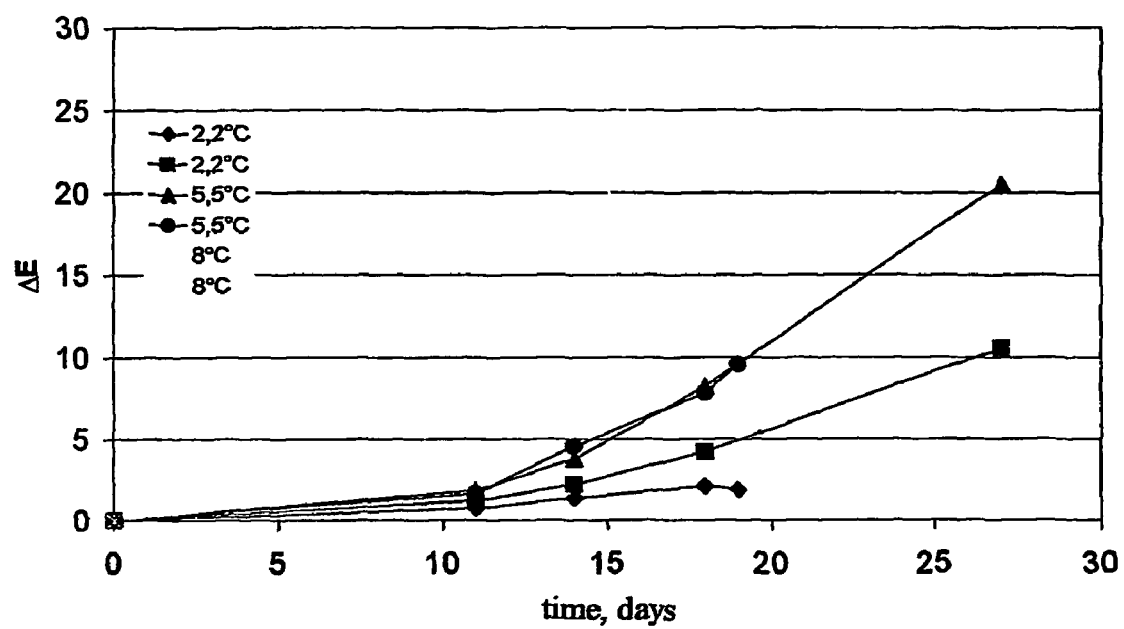
FIG. 1 is a graphic representation of the values of table 3.
Figure 2:
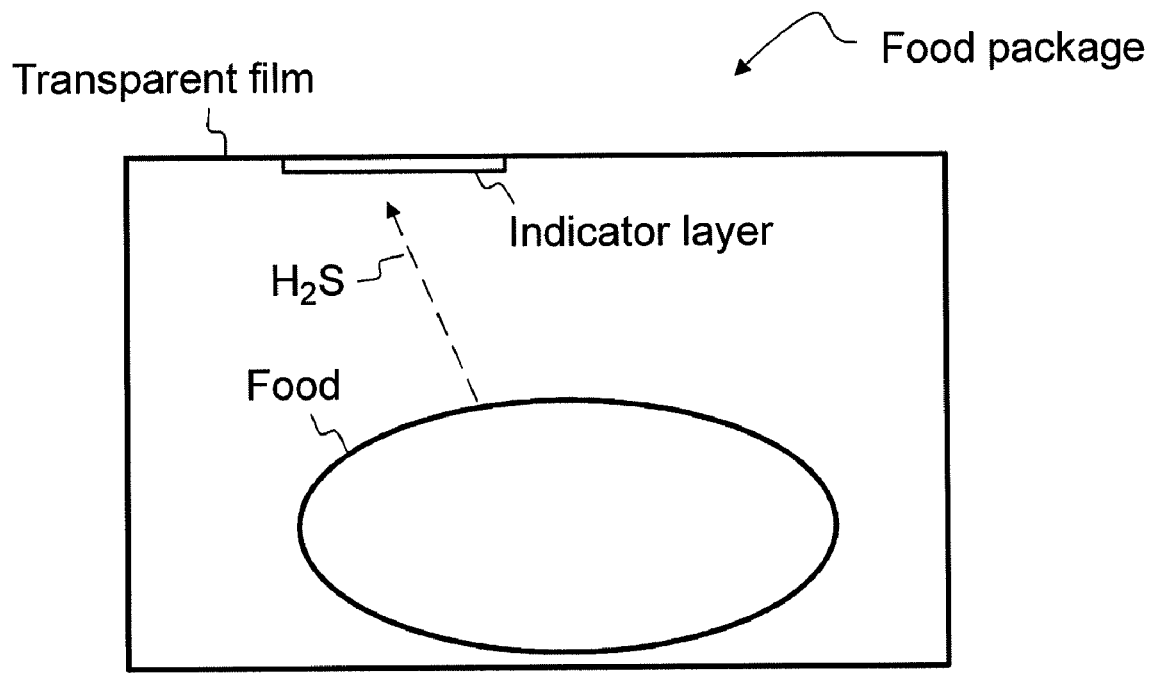
FIG. 2 illustrates an indicator layer attached to a package by an adhesive label.
Figure 3:
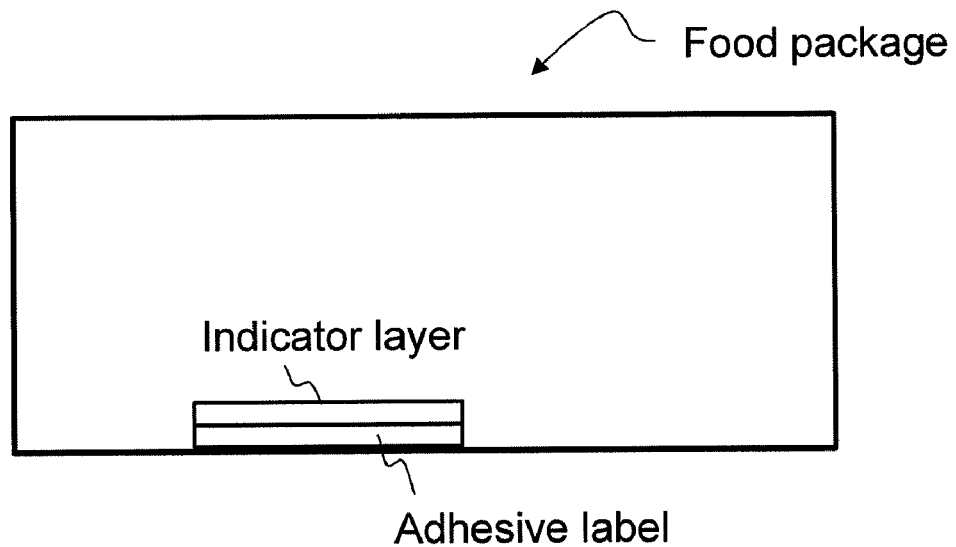
FIG. 3 illustrates an indicator layer arranged on a transparent film, which is used as the top of a food package.

The indicator according to the invention has, for example, the following advantages:

Because the colour change in the indicator is visible to the eyes, no special equipment will be needed for monitoring it. However, it is possible to use automatic monitoring devices for analysing the change in the colour. In a given gas concentration, an abrupt, visually detectable change takes place in the colour of the indicator. The change in the colour can be adjusted to a given concentration. In tests carried out, it was observed that the change in the colour can be made to take place in a reproducible way; in other words, the indicator can be made very reliable.

The indicator according to the invention is arranged to react to gaseous substances, particularly hydrogen sulphide. The indicator can be used to indicate a gas concentration which presents odour problems to the environment or a hazard for persons working in the facilities. Furthermore, the indicator can be utilized in the maintenance of industrial plants, wherein an increase in gas concentrations can be used to trace, for example, a leak in the process equipment. The indicator can also be used to monitor the concentration of hydrogen sulphide in facilities where it would be harmful to expose equipment, particularly electrical devices, to cold corrosion. Uses of the indicator include, for example, water treatment plants (particularly biological sewage treatment plants), sewer systems, dumping areas, and equipment facilities in the processing industry. The indicator can also be used for controlling the purity of air in houses and places of work.

When the gas to be detected is hydrogen sulphide, the indicator can be set to indicate, for example, maximum hydrogen sulphide concentrations given by various guidelines:

- 14 $g/m^3$ (10 ppm), the concentration known to be harmful after an exposure of 8 h;
- 21 $g/m^3$ (15 ppm), the concentration known to be harmful after an exposure of 15 min;
- 0.011 $g/m^3$ (0.008 ppm), the concentration detectible by the sense of smell;
- 0.005 ppm, the WHO guideline not to be exceeded by the concentration in the air,
- 0.1 ppm, maximum temporary health hazard for 60 minutes (ERPG-1);
- 30 ppm, without serious health hazards for 60 minutes (ERPG-2);
- 100 ppm, without danger to life for 60 minutes (ERPG-3).

The indicator according to the invention can be used, for example, as an indicator of shelf life, wherein in small quantities of substances indicating decaying, an abrupt change takes place in the colour of the indicator, wherein the indicator can be monitored, for example, in a retail shop or under household conditions. The indicator reacts chemically with substances evaporated from the decaying product in such a way that the colour of the indicator is changed.

The change in the colour of the indicator takes place in a reliable (reproducible) way in relation to the quantity of the substances indicating decaying of the decayable product.

In the following, the invention will be discussed particularly for the use as an indicator of shelf life in food packages, but the indicator according to the invention can also be applied to other uses, made in the same way and reacting to the same gases. However, indicators made as such by the same principle must be adjusted, in their parameters, to the use; for example, the gas concentration in which the change in the colour of the indicator takes place, must be adjusted in view of the requirements of the use.

The shelf life indicator can be manufactured on a separate substrate to be easily attached to a package, such as a self-adhesive label, or the manufacture of the shelf life indicator can be directly integrated in the manufacture of the food packages; in other words, the indicator can be made in connection with the manufacture of the package material and, for example, any separate steps to attach the shelf life indicator in connection with the packing will not be needed.

Metallic silver has been approved for use in connection with foodstuffs, also in direct contact. Moreover, there is a long experience of the use of metallic silver with foodstuffs; it has been used in cutlery and serving dishes for a long time.

The indicator according to the invention is used particularly in uses requiring an indicator reacting to volatile sulphur compounds. The indicator according to the invention can be used as a shelf life indicator in food packages intended for the packing of foodstuffs which, when decaying, produce chemical compounds, for example sulphur compounds, such as hydrogen sulphide, dimethyl sulphide and/or dimethyl disulphide. The composition of the chemical compounds volatilizing from decaying food depends on the food in question. Sulphur compounds are produced particularly in the decaying of poultry meat, such as chicken or turkey. The chemical compound may also be other than a sulphur compound, as long as it reacts with metallic silver and/or copper, causing a change in the colour.

The food may be packed without a shielding gas, the package may contain a shielding gas, such as a nitrogen or carbon dioxide shielding gas or a shielding gas containing both of said shielding gases, or the product may be packed in a vacuum. The shelf life indicator is inside the package, that is, in a space where it can react with the sulphur compound emitted from the decaying food. The shelf life indicator comprises a metal which is selected from the group of transition elements and is preferably of metallic silver and/or copper. When the metal reacts with hydrogen sulphide, sulphides are produced. The chemical reaction with the sulphur compound results in a relatively abrupt change in the colour of the shelf life indicator, which correlates well with the quantity of the sulphur compound emitted into the package, such as hydrogen sulphide, dimethyl sulphide and/or dimethyl disulphide.

The indicator is made either by applying a metal layer on a suitable non-metal substrate or by printing, it on a suitable printing base, for example by the screen printing or the flexographic printing technique. The printing base can be, for example, paper, board, or plastic. The printing paste comprises at least an adhesive and metal particles with an average diameter of preferably less than 10 μm. Advantageously, the printing paste contains metal particles 70 to 90 percent of the dry substance of the printing paste. Suitable adhesives to be used in flexographic printing include, for example, shellac, cellulose nitrate, ethyl cellulose, cellulose acetate propionate (CAP), polyamide resins, acrylic and methacrylic resins, ketone resins, polyvinyl acetate, and polyvinyl chloride. Suitable adhesives to be used in screen printing include, for example, acrylic, polyurethane and vinyl resins.

When a metal coating is applied on a non-metallic substrate, for example by vapour deposition or sputtering, it can be made very thin, normally with a layer thickness of 1 to 10 nm. An advantageous layer thickness is 1 to 5 nm.

The metal layer to be applied either by printing, sputtering or vapour deposition can be made, for example, on a transparent plastic film to be used as the top of a food package, wherein the shelf life indicator remains inside the food package but can be observed from the outside of the package. Advantageously, the metal layer covers the plastic film for only a given part; that is, the indicator may be relatively small in size when compared with a plastic film top. The colour of the thin metal layer is changed throughout, wherein said embodiment is very handy. For example, in a silver layer with the thickness of 1 nm, a distinct change was observed in the colour by the effect of hydrogen sulphide in the concentration of 0.016 mg/l (silver film applied on a polyester or polycarbonate film).

The sensitivity of the shelf life indicator can be adjusted e.g. by changing the thickness of the metal layer. As the layer thickness is increased, the change in the colour takes place in a higher gas concentration. The sensitivity of the indicator is also affected by the quality of the material onto whose surface the indicator layer is applied.

Example 1

Chicken fillet slices (about 115±5 g) were packed in 210 ml box packages (material HDPE) with a shielding gas (80% $CO_2$/20% $N_2$) and stored at a constant temperature of +5.5° C. and +8° C.

For the analysis of volatile metabolites, a 5 ml gas sample was taken with a gas-tight syringe from the gas space of the packages and injected into a head-space flask (volume 22 ml) sealed in a gas-tight manner in a clean room. The hydrogen sulphide concentrations in the gas space were determined by gas chromatography by using a sulphur selective detector.

The hydrogen sulphide concentration of the gas space increased as a function of the storage time and temperature (table 1) and represented the shelf life of the chicken slices.

TABLE 1

Hydrogen sulphide concentration (mg/l) in the gas space of chicken fillet slices stored at different temperatures [1].

| Storage time (days) | $H_2S$ concentration (mg/l) in gas space, storage temperature +5.5° C. | $H_2S$ concentration (mg/l) in gas space, storage temperature +8° C. |
|---|---|---|
| 0 | no observation | no observation |
| 5 | no observation | no observation |
| 7 | no observation | + |
| 9 | + | 0.2 |
| 12 | 0.15 | 0.75 |

[1] The quantizability limit in the test is 0.1 ml/l; no obersvation = no observable peak in the chromatograph, + = a detectable peak below the quantizability limit in the chromatograph. The number of parallel tests was 2.

Example 2

TABLE 2

Change in the colour of a silver indicator made by flexographic printing in a reaction with hydrogen sulphide (measured by X-rite densitometer).

| Hydrogen sulphide concentration (mg/l) | Darkness in colour of indicator (in $O_2$) | Darkness in colour of indicator (in $N_2$) |
|---|---|---|
| 0 | 0.32 | 0.31 |
| 0.03 | 0.51 | 0.43 |
| 0.08 | 0.57 | 0.45 |
| 0.16 | 0.61 | 0.48 |
| 1.6 | 0.63 | 0.48 |
| 3.2 | 0.63 | 0.52 |

Example 3

Table 3 shows, as a function of time, the change in the colour of shelf life indicators made by flexographic printing and placed in the gas spaces of turkey packages stored at different temperatures. ΔE=total index of the change in the colour of the indicators, measured in a scale of L,a,b and calculated from the formula $\Delta E=(\Delta L^2+\Delta a^2+\Delta b^2)^{1/2}$. The shielding gas used in the food packages was carbon dioxide. The values of table 3 are shown graphically in FIG. 1.

TABLE 3

Change in the colour of shelf life indicators as a function of time.

| Temperature/sample | Colour change (ΔE) Storage time/d | | | | | | |
|---|---|---|---|---|---|---|---|
| | 0 | 7 | 11 | 14 | 18 | 19 | 27 |
| 2.3° C./sample A | 0 | | 0.8 | 1.4 | 2.1 | 1.9 | |
| 2.3° C./sample B | 0 | | 1.2 | 2.2 | 4.2 | | 10.6 |
| 5.5° C./sample C | 0 | | 1.8 | 3.8 | 8.2 | | 20.6 |
| 5.5° C./sample D | 0 | | 1.7 | 4.6 | 7.8 | 9.6 | |
| 8.3° C./sample E | 0 | 1.9 | 6.9 | 19.2 | 22.3 | | |
| 8.3° C./sample F | 0 | 1.4 | 20.2 | 23.3 | 27.5 | | |

Example 4

TABLE 4

Change in the colour of silver indicators made by sputtering, in a reaction with hydrogen sulphide (measured by X-rite densitometer).

| Hydrogen sulphide concentration (mg/l) | Indicator colour/darkness (reaction in air) | |
|---|---|---|
| | 1 nm film on polycarbonate | 3 nm film on pigment-coated polycarbonate |
| 0 | 0.41 (pink) | 0.80 (dark grey) |
| 0.016 | 0.33 (colourless) | 0.54 (light grey) |
| 0.03 | 0.33 (colourless) | 0.52 (light grey) |
| 0.08 | 0.33 (colourless) | 0.39 (yellow) |
| 0.16 | 0.32 (colourless) | 0.36 (yellow) |
| 3.2 | 0.31 (colourless) | 0.41 (yellow) |

Example 5

TABLE 5

Hydrogen sulphide concentration in the gas spaces of packages of chicken slices packed in shielding gas and stored at various temperature conditions, and the perceivable acceptability of the slices

| Storage temperature (mean) (° C.) | Storage time (days) | Hydrogen sulphide concentration in gas space (μg/l) | Perceivable acceptability of product |
|---|---|---|---|
| 3.4 | 9 | ≦5* | Acceptable |
| 6.5 | 9 | 1300 | Unacceptable |
| 8.3 | 9 | 2000 | Clearly unacceptable |
| 3.4 | 12 | ≦5* | Acceptable |
| 6.5 | 12 | 5500 | Clearly unacceptable |
| 8.3 | 12 | 10000 | Clearly unacceptable |

*Detection limit of the GC method

TABLE 6

Hydrogen sulphide concentration and sulphurous odour in the gas space of the package of turkey slices packed in shielding gas and stored at various temperature conditions, as well as change in the colour of indicators based on a silver film (sputtered silver film of about 1 nm) attached to the gas space of the package.

| Storage temperature (mean) (° C.) | Storage time (days) | Hydrogen sulphide concentration in gas space (μg/l) | Sulphurous odour | Change in indicator colour |
|---|---|---|---|---|
| 3.0 | 11 | <1* | No | No |
| 3.0 | 14 | <1* | No | No |
| 3.0 | 18 | <1* | No (package A) Yes (package B) | No (package A) Yes (package B) |
| 7.9 | 11 | 2.5 (package A) 5.5 (package B) | Yes | Yes |
| 7.9 | 12 | 4 (package A) | Yes | Yes |

*Detection limit of the GC method

Example 6

Various hydrogen sulphide indicators based on a thin silver film were compared for their sensitivity in the change of colour to low concentrations of hydrogen. The indicators which contained silver were applied on two different films (PET, PP), and two different thicknesses of the indicator layer were used (1 nm, 2 nm).

The indicator samples were: 1. PET 1 nm, 2. PET 2 nm, 3. PP 1 nm, and 4. PP 2 nm.

The indicators were attached to the inside of the top film in 600 ml packages, and the boxes were packed by rinsing with a shielding gas. The composition of the shielding gas was 9.5% of $O_2$, 90.5% of $CO_2$, 100 ppm hydrogen was added into the packages, according to table 7. Next, the changes in the colour of the different indicators were compared. The colour of the indicators was evaluated visually. In particular, the aim was to compare different indicator materials with each other.

The results from the comparison in the sensitivity of the indicators are shown in table 8. Distinct differences were observed in the rate and completeness of the change in the colour of the indicators. The indicator was printed in the shape of a cross. When the indicator reacted with the gas, the cross was highlighted from the rest of the printing.

With the lowest examined $H_2S$ concentration (0.1 μg/l), an incipient change in the colour was observed in the indicators 1 and 2 made on a PET film in only less than an hour after the addition of hydrogen sulphide. Also, in the indicator 3 made of a PP film, a change in the colour was observed relatively soon (1.3 h from the starting of the reaction). The 2 nm indicator 4 made of another PP film did not react until 1 day from the addition of hydrogen sulphide. In the lowest concentration, the final change in the colour was most distinct in the indicators 1, 2 and 3.

In the lowest $H_2S$ concentration of 0.5 μg/l, an incipient change in the colour was observed in the indicators 1 and 2 made of a PET film in only 15 minutes after the addition of hydrogen sulphide. In the indicator 3 made of a PP film, a change in the colour was observed relatively soon (35 min after starting the reaction). Also, the 2 nm indicator 4 made by using a thicker PP film reacted in 35 minutes but to a clearly lesser extent than the indicator 3.

In the $H_2S$ concentration of 0.9 μg/l, an incipient change in the colour was observed in the indicators 1 and 2 made of a PET film and in the indicator 3 made of a PP film in only 10 minutes after the addition of hydrogen sulphide. The 2 nm indicator 4 made by using the thicker PP film reacted in about 30 minutes in such a way that the cross in the indicator became distinguishable.

In the highest tested $H_2S$ concentration (4.7 μg/l), a complete change in the colour was observed in all the tested indicators in only about 2.5 hours after the addition of hydrogen sulphide. In the indicators 1 and 2 made of a PET film, the colour change started in only 0.5 minutes after the addition of hydrogen sulphide. For example, in 3 minutes after the addition of hydrogen sulphide, the 2 nm indicator 4 made by using a PP film had reacted by becoming clearly lighter at the edges.

On the basis of the results, it could be concluded that the indicators 1 and 2 made of a PET film were the fastest ones to react of the indicators tested. The 1 nm indicator 3 made of a PP film was slightly slower than these to react. The indicator 4 (PP/2 nm) had the slowest reaction. In the final colour change of the indicators, differences could be found primarily in the lowest test concentration (0.1 μg/l) of hydrogen sulphide. The difference was manifested in the size of the reaction area in the indicator. The largest reaction areas were found for the indicators 1, 2 and 3. The reaction area of indicator 4 was clearly smaller. In the other tested concentrations of hydrogen sulphide, the reaction of the indicators was virtually complete after the reaction of 2 days.

TABLE 7

Additions of hydrogen sulphide

| Indicator | Sample package | Final $H_2S$ concentration in package (μg/l) | Addition of 100 ppm $H_2S$ |
|---|---|---|---|
| 1. | 1, 2 | 0 | — |
| 2. | 3, 4 | 0 | — |
| 3. | 5, 6 | 0 | — |
| 4. | 7, 8 | 0 | — |
| 1. | 11, 12 | 0.093 | 400 μl |
| 2. | 13, 14 | 0.093 | 400 μl |
| 3. | 15, 16 | 0.093 | 400 μl |
| 4. | 17, 18 | 0.093 | 400 μl |
| 1. | 21, 22 | 0.47 | 2 ml |
| 2. | 23, 24 | 0.47 | 2 ml |
| 3. | 25, 26 | 0.47 | 2 ml |
| 4. | 27, 28 | 0.47 | 2 ml |
| 1. | 31, 32 | 0.93 | 4 ml |
| 2. | 33, 34 | 0.93 | 4 ml |
| 3. | 35, 36 | 0.93 | 4 ml |
| 4. | 37, 38 | 0.93 | 4 ml |
| 1. | 41, 42 | 4.7 | 20 ml |
| 2. | 43, 44 | 4.7 | 20 ml |
| 3. | 45, 46 | 4.7 | 20 ml |
| 4. | 47, 48 | 4.7 | 20 ml |

TABLE 8

Visual evaluation of the colour of the indicators.

| Indicator | Samples | Evaluation of the colour change | | |
|---|---|---|---|---|
| $H_2S$ 0 μg/l | | No change in the colour of the indicators within two days. | | |
| 1. | 1, 2 | | | |
| 2. | 3, 4 | | | |
| 3. | 5, 6 | | | |
| 4. | 7, 8 | | | |
| $H_2S$ 0.1 μg/l | | 20 min after the addition of $H_2S$ | 40 min after the addition of $H_2S$ | 1 d after the addition of $H_2S$ |
| 1. | 11, 12 | no change | indicator edges slightly lighter | light edges in the cross in the indicator |
| 2. | 13, 14 | no change | indicator edges slightly lighter | light edges in the cross in the indicator |
| 3. | 15, 16 | no change | no detectable change | light edges in the cross in the indicator (less than 11 to 14) |
| 4. | 17, 18 | no change | no detectable change | light edges in the cross in the indicator (less than 15 to 16) |
| $H_2S$ 0.5 μg/l | | 15 min after the addition of $H_2S$ | 35 min after the addition of $H_2S$ | 1 d after the addition of $H_2S$ |
| 1. | 21, 22 | a sliver of light in the edges of the indicator | a clear change in the indicator | changeable areas completely changed |
| 2. | 23, 24 | a sliver of light in the edges of the indicator | a clear change in the indicator | changeable areas completely changed |
| 3. | 25, 26 | no change | a sliver of light in the edges of the indicator, change slightly smaller than in 21 to 24 | changeable areas are light, also part of the cross is lighter |
| 4. | 27, 28 | no change | a sliver of light in the edges of the indicator, change clearly smaller than in 25 to 26 | changeable areas of the indicator are light, a small dark point at the upper edge |
| $H_2S$ 0.9 μg/l | | 10 min after the addition of $H_2S$ | 30 min after the addition of $H_2S$ | 1 d after the addition of $H_2S$ |
| 1. | 31, 32 | edges of the indicator are slightly changed | indicator almost completely changed | indicator completely changed |
| 2. | 33, 34 | edges of the indicator are slightly changed | indicator almost completely changed | indicator completely changed |
| 3. | 35, 36 | edges of the indicator are slightly changed | edges of the indicator are changed, also the cross is lighter | indicator is almost completely light, also the cross is lighter |

TABLE 8-continued

Visual evaluation of the colour of the indicators.

| Indicator | Samples | Evaluation of the colour change | | |
|---|---|---|---|---|
| 4. | 37, 38 | no change | edges of the indicator are changed, cross is distinguishable in one of two specimens | one of two specimens completely changed, one having a small dark point |

The invention is not restricted to the description above, but it may vary within the scope of the claims. The examples presented only discuss metallic silver which is a particularly advantageous choice of metal, but the metal can also be copper or a mixture of silver and copper, or a layered structure.

The invention claimed is:

1. A package for enclosing a food product, the package comprising:
a layer configured to change color when reacting with gaseous hydrogen sulfide emitted from the food product, wherein the layer comprises metallic silver, and wherein a thickness of the layer is less than or equal to 10 nm.

2. The package according to claim 1, further comprising:
an indicator comprising the layer and a substrate which is a self-adhesive label.

3. The package according to claim 2, wherein the substrate comprises a plastic film.

4. The package according to claim 1, wherein said layer is visually observable through a shell of said package.

5. The package according to claim 1, wherein said layer is a silver layer.

6. The package according to claim 5, wherein said layer is arranged on a transparent plastic film.

7. The package according to claim 5, wherein said layer is arranged on a polyester film.

8. The package according to claim 1, wherein said layer is arranged on a PET film.

9. The package according to claim 1, wherein said package has a shape which is configured to become visually distinguishable after the layer has reacted with hydrogen sulfide.

10. The package according to claim 1, further comprising:
an indicator comprising the layer, wherein a color of the indicator is configured to become lighter when the layer reacts with hydrogen sulfide.

* * * * *